(12) United States Patent
Peterson et al.

(10) Patent No.: US 8,918,179 B2
(45) Date of Patent: Dec. 23, 2014

(54) SYSTEM AND METHOD FOR INCREASING RELATIVE INTENSITY BETWEEN CATHODES AND ANODES OF NEUROSTIMULATION SYSTEM

(71) Applicant: Boston Scientific Neuromodulation Corporation, Valencia, CA (US)

(72) Inventors: David K. L. Peterson, Valencia, CA (US); Kerry Bradley, Glendale, CA (US); Jan Holsheimer, Oldenzaal (NL)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 14/155,035

(22) Filed: Jan. 14, 2014

(65) Prior Publication Data
US 2014/0128956 A1 May 8, 2014

Related U.S. Application Data

(63) Continuation of application No. 13/937,035, filed on Jul. 8, 2013, now Pat. No. 8,660,655, and a continuation of application No. 12/508,407, filed on Jul. 23, 2009, now Pat. No. 8,494,640.

(60) Provisional application No. 61/084,208, filed on Jul. 28, 2008.

(51) Int. Cl.
*A61N 1/00* (2006.01)
*A61N 1/05* (2006.01)
*A61N 1/36* (2006.01)

(52) U.S. Cl.
CPC ............ *A61N 1/0551* (2013.01); *A61N 1/0553* (2013.01); *A61N 1/3605* (2013.01); *A61N 1/36157* (2013.01)

USPC .......................................................... 607/46

(58) Field of Classification Search
USPC .......................................................... 607/46
See application file for complete search history.

(56) References Cited

U.S. PATENT DOCUMENTS

| 3,822,708 | A | 7/1974 | Zilber |
| 4,602,624 | A | 7/1986 | Naples et al. |

(Continued)

FOREIGN PATENT DOCUMENTS

| EP | 2 002 861 A2 | 12/2008 |
| EP | 2 077 135 A2 | 7/2009 |
| EP | 1 904 161 B1 | 10/2009 |

OTHER PUBLICATIONS

PCT International Search Report for PCT/US2009/051584, Applicant: Boston Scientific Neuromodulation Corporation, Form PCT/ISA/210 and 220, dated Oct. 19, 2009 (7 pages).

(Continued)

*Primary Examiner* — Robert N Wieland
(74) *Attorney, Agent, or Firm* — Vista IP Law Group LLP

(57) ABSTRACT

A method and neurostimulation system for providing therapy to a patient is provided. A plurality of electrodes is placed adjacent to tissue of the patient. The electrodes include first and second electrodes, with the first electrode having a first tissue contacting surface area and the second electrode having a second tissue contact surface area greater than the first tissue contacting surface area. Anodic electrical current is simultaneously sourced from one of the first and second electrodes to the tissue and while cathodic electrical current is sunk from the tissue to another of the first and second electrodes to provide the therapy to the patient.

10 Claims, 9 Drawing Sheets

(56) References Cited

U.S. PATENT DOCUMENTS

| | | | |
|---|---|---|---|
| 5,643,330 | A | 7/1997 | Holsheimer et al. |
| 5,755,750 | A | 5/1998 | Petruska et al. |
| 6,236,892 | B1 | 5/2001 | Feler |
| 6,895,280 | B2 | 5/2005 | Meadows et al. |
| 7,031,777 | B2 * | 4/2006 | Hine et al. ............... 607/122 |
| 7,379,775 | B2 | 5/2008 | Parramon et al. |
| 7,496,404 | B2 | 2/2009 | Meadows et al. |
| 7,551,964 | B2 | 6/2009 | Dobak, III |
| 7,684,866 | B2 * | 3/2010 | Fowler et al. ............... 607/45 |
| 2004/0044379 | A1 | 3/2004 | Holsheimer |
| 2007/0100378 | A1 | 5/2007 | Maschino |
| 2007/0142863 | A1 | 6/2007 | Bradley |
| 2007/0150036 | A1 | 6/2007 | Anderson |
| 2007/0168004 | A1 | 7/2007 | Walter |
| 2007/0168007 | A1 | 7/2007 | Kuzma et al. |
| 2007/0179579 | A1 | 8/2007 | Feler et al. |
| 2007/0203544 | A1 | 8/2007 | Goetz et al. |
| 2008/0009927 | A1 | 1/2008 | Vilims |
| 2008/0161895 | A1 | 7/2008 | Gross et al. |
| 2008/0183264 | A1 | 7/2008 | Bly et al. |
| 2008/0208293 | A1 | 8/2008 | Parramon et al. |
| 2009/0018620 | A1 | 1/2009 | Bernabe et al. |
| 2009/0204174 | A1 | 8/2009 | Parramon et al. |
| 2009/0276021 | A1 | 11/2009 | Meadows et al. |
| 2009/0287279 | A1 | 11/2009 | Parramon et al. |
| 2012/0029582 | A1 | 2/2012 | Ayal et al. |

OTHER PUBLICATIONS

PCT Written Opinion of the International Search Authority for PCT/US2009/051584, Applicant: Boston Scientific Neuromodulation Corporation, Form PCT/ISA/237, dated Oct. 19, 2009 (7 pages).

PCT International Preliminary Report on Patentability (Chapter I of the Patent Cooperation Treaty) for PCT/US2009/051584, Applicant: Boston Scientific Neuromodulation Corporation, Form PCT/IB/326 and 373, dated Feb. 10, 2011 (9 pages).

* cited by examiner

SYSTEM AND METHOD FOR INCREASING RELATIVE INTENSITY BETWEEN CATHODES AND ANODES OF NEUROSTIMULATION SYSTEM

RELATED APPLICATION DATA

The present application is a continuation of U.S. patent application Ser. No. 13/937,035, filed Jul. 8, 2013, now issued as U.S. Pat. No. 8,660,665, which is a continuation of U.S. patent application Ser. No. 12/508,407, filed Jul. 23, 2009, now issued as U.S. Pat. No. 8,494,640, which claims the benefit under 35 U.S.C. §119 to U.S. provisional patent application Ser. No. 61/084,208, filed Jul. 28, 2008. The foregoing applications are expressly incorporated herein by reference.

FIELD OF THE INVENTION

The present invention relates to tissue stimulation systems, and more particularly, to a system and method for conditioning and stimulating nerve fibers.

BACKGROUND OF THE INVENTION

Implantable neurostimulation systems have proven therapeutic in a wide variety of diseases and disorders. Pacemakers and Implantable Cardiac Defibrillators (ICDs) have proven highly effective in the treatment of a number of cardiac conditions (e.g., arrhythmias). Spinal Cord Stimulation (SCS) systems have long been accepted as a therapeutic modality for the treatment of chronic pain syndromes, and the application of tissue stimulation has begun to expand to additional applications such as angina pectoralis and incontinence. Deep Brain Stimulation (DBS) has also been applied therapeutically for well over a decade for the treatment of refractory chronic pain syndromes, and DBS has also recently been applied in additional areas such as movement disorders and epilepsy. Further, in recent investigations, Peripheral Nerve Stimulation (PNS) systems have demonstrated efficacy in the treatment of chronic pain syndromes and incontinence, and a number of additional applications are currently under investigation. Furthermore, Functional Electrical Stimulation (FES) systems, such as the Freehand system by NeuroControl (Cleveland, Ohio), have been applied to restore some functionality to paralyzed extremities in spinal cord injury patients.

Each of these implantable neurostimulation systems typically includes one or more electrode carrying stimulation leads, which are implanted at the desired stimulation site, and a neurostimulator implanted remotely from the stimulation site, but coupled to the stimulation lead(s). Thus, electrical pulses can be delivered from the neurostimulator to the stimulation lead(s) to stimulate or activate a volume of neural tissue. In particular, electrical energy conveyed between at least one cathodic electrode and at least one anodic electrodes creates an electrical field, which when strong enough, depolarizes (or "stimulates") the neurons beyond a threshold level, thereby inducing the firing of action potentials (APs) that propagate along the neural fibers.

Stimulation energy may be delivered to the electrodes during and after the lead placement process in order to verify that the electrodes are stimulating the target neural elements and to formulate the most effective stimulation regimen. The regimen will dictate which of the electrodes are sourcing current pulses (anodes) and which of the electrodes are sinking current pulses (cathodes) at any given time, as well as the magnitude and duration of the current pulses. The stimulation regimen will typically be one that provides stimulation energy to all of the target tissue that must be stimulated in order to provide the therapeutic benefit, yet minimizes the volume of non-target tissue that is stimulated. In the case of SCS, such a therapeutic benefit is "paresthesia," i.e., a tingling sensation that is effected by the electrical stimuli applied through the electrodes.

While the electrical stimulation of neurons has generally been successful in providing a therapeutic benefit to the patient, there are instances where the target tissue is not directly adjacent to an electrode and, because the electrical field strength decreases exponentially with distance from the electrodes, a relatively strong electrical field must be created to generate APs in the target neural fibers. The electrical field may, however, also result in the generation of APs in the non-target neural fibers between the electrode and the target neural fibers. The generation of APs in the non-target neural fibers may, in turn, lead to undesirable outcomes (e.g., discomfort or involuntary movements) for the patient. Because the target neural tissue (i.e., the tissue associated with the therapeutic effects) and non-target neural tissue (i.e., the tissue associated with undesirable side effects) are often juxtaposed, therapeutically stimulating neural tissue while preventing side effects may be difficult to achieve. In the context of SCS, there may be a few ways of eliminating, or at least minimizing, the stimulation of non-target neural tissue.

For example, in the case where the electrode array is medio-laterally aligned (i.e., the electrodes are arranged transversely to the neural fibers of the spinal cord), it may be desirable to control the shape of the AP generating neural region of the spinal cord in order to prevent the generation of APs in non-target neural fibers. For example, to produce the feeling of paresthesia without inducing involuntary motor movements within the patient, it is often desirable to preferentially stimulate nerve fibers in the dorsal column (DC nerve fibers), which primarily include sensory nerve fibers, over nerve fibers in the dorsal roots (DR nerve fibers), which include both sensory nerve fibers and motor reflex nerve fibers. While DC nerve fibers are the intended targets in conventional SCS, in fact, the DR nerve fibers often are recruited first because of geometric, anatomical, and physiological reasons. For example, the DR nerve fibers have larger diameters than the largest nearby DC nerve fibers, and thus, have a lower threshold at which they are excited. Other factors that contribute to the lower threshold needed to excite DR nerve fibers are the different orientations of the DC nerve fibers and DR nerve fibers, the curved shape of the DR nerve fibers, and the inhomogeneity and anisotropy of the surrounding medium at the entrance of the DR nerve fibers into the spinal cord. Thus, DR nerve fibers may still generate APs at lower voltages than will nearby DC nerve fibers. As a result, the DC nerve fibers that are desired to be stimulated have a lower probability to be stimulated than do the DR nerve fibers, and thus, the reflex motor nerve fibers intermingled among the sensor nerve fibers of a dorsal root are often recruited, leading to discomfort or muscle twitching, thereby preventing satisfactory paresthesia coverage.

For reasons such as these, it is often desirable to modify the threshold at which neural tissue is activated in a manner that maximizes excitation of the target neural tissue, while minimizing excitation of the non-target neural tissue; that is, to increase the DR/DC threshold ratio. This can be accomplished by sinking an electrical pulse to a cathodic electrode located at the center of the spinal cord to depolarize the target tissue adjacent the cathodic electrode, thereby creating APs along the DC nerve fibers, while an electrical pulse can be sourced to anodic electrodes on both sides of the cathodic electrode to hyperpolarize non-target tissue adjacent the anodic electrodes, thereby increasing the threshold of the DR nerve fibers.

As another example, in the case where the electrode array is rostro-caudally aligned (i.e., the electrodes are arranged along the neural fibers of the spinal cord), it may be desirable to induce APs in a bundle of target nerve fibers, and to the extent that APs are induced in bundle of non-target nerve fibers, block APs within the non-target nerve fibers from reaching the brain or any other parts of the nervous system. In particular, an electrical pulse can be sunk to a cathodic electrode to depolarize target tissue adjacent the cathodic electrode, thereby creating APs along a first bundle of nerve fibers, while an electrical pulse can be sourced to one or more anodic electrodes above or below the cathodic electrode to hyperpolarize non-target tissue adjacent the anodic electrode(s), thereby blocking any APs along a second bundle of nerve fibers that were inadvertently induced by the sink electrical pulse of the cathodic electrode.

Because the amount of electrical current that is sourced must equal the amount of electrical current that is sunk, the amount of sourced electrical current must be limited in order to minimize the adverse effects that could potentially occur as a result of the increased amount of the sunk electrical current. For example, in the previously described case where the electrode array is rostro-caudally aligned, an increase in the electrical current sunk by the cathode as a result of an increase in the electrical current sourced by the anodes(s) may result in the generation of APs in non-target nerve fibers that are not blocked by the sourced electrical current. In the previously described case where the electrode array is medio-laterally aligned, an increase in the electrical current sunk by the cathode as a result of an increase in the electrical current sourced by the anodes may result in the generation of APs in non-target DC nerve fibers.

To limit the amount of current sunk by a cathode, it is known to redistribute some of the cathodic current to a large surface area, such as the case of the IPG. Such a technique is described in U.S. patent application Ser. No. 11/300,963, entitled "Apparatus and Methods for Stimulating Tissue," which is expressly incorporated herein by reference. By distributing the cathodic current to a surface area that has no, or very little, effect on the neural tissue, the magnitude of the electrical pulses sourced by the anodes can be increased while avoiding a commensurate increase in the magnitude of the electrical pulses sunk to the cathode that is adjacent the neural tissue. In this manner, any adverse effects that may otherwise occur as a result of an increase in the electrical current sunk to the cathodic electrode, and thus conveyed through the neural tissue adjacent the cathodic electrode, can be minimized.

While this electrical current redistribution technique is beneficial, it can only be implemented within an IPG that has independent current or voltage sources for the electrodes. That is, an IPG with a single current or voltage source provides no means for redistributing a selected amount of cathode current to the IPG case.

There, thus, remains a need for an alternative neurostimulation method and system that minimizes any adverse effects that may result in an increase in cathodic current when the anodic current is increased.

SUMMARY OF THE INVENTION

In accordance with a first aspect of the present inventions, a method of providing therapy to a patient is provided. The method comprises placing a plurality of electrodes adjacent to tissue of the patient. The electrodes include first and second electrodes, with the first electrode having a first tissue contacting surface area and the second electrode having a second tissue contact surface area greater than (e.g., at least twice) the first tissue contacting surface area.

The method further comprises simultaneously sourcing anodic electrical current from one of the first and second electrodes (e.g., the first electrode) to the tissue and sinking cathodic electrical current from the tissue to another of the first and second electrodes (e.g., the second electrode) to provide the therapy to the patient. In one method, the anodic electrical current and cathodic electrical current take the form of electrical pulses. In another method, the size disparity between the first and second tissue contacting surfaces causes the current density on the first tissue contacting surface to be greater than the current density on the second tissue contacting surface.

The tissue to which the electrodes are placed adjacent can be, e.g., spinal cord tissue. In one method, the electrodes are arranged medio-laterally along the spinal cord tissue. In this case, the second electrode can be adjacent to dorsal column neural fibers of the spinal cord tissue, the first electrode can be adjacent to dorsal root neural fibers of the spinal cord tissue, the sunk cathodic electrical current can generate action potentials in the dorsal column neural fibers of the spinal cord tissue, and the sourced anodic electrical current can increase the action potential threshold of the dorsal root neural fibers. In another exemplary method, the electrodes are arranged rostro-caudally along the spinal cord tissue. In this case, the second electrode can be a first distance from the first neural fiber bundle and a second greater distance from the second neural fiber bundle, the sunk cathodic electrical current can generate action potentials in the first and second neural fibers bundles, and the sourced anodic electrical current can block at least some of the action potentials in the first neural fiber bundle.

In accordance with a second aspect of the present inventions, a neurostimulation system is provided. The neurostimulation system comprises a plurality of electrodes configured for being placed adjacent to tissue of a patient. The electrodes include first and second electrodes, with the first electrode having a first tissue contacting surface area and the second electrode having a second tissue contact surface area greater than (e.g., at least twice) the first tissue contacting surface area.

The neurostimulation system further comprises output stimulation circuitry coupled to the plurality of electrodes. The output stimulation circuitry is configured for sourcing anodic electrical current to one of the first and second electrodes (e.g., the first electrode) and sinking cathodic electrical current from another of the first and second electrodes (e.g., the second electrode) to provide therapy to the patient. In one embodiment, the anodic electrical current and cathodic electrical current take the form of electrical pulses. In another embodiment, the size disparity between the first and second tissue contacting surfaces is such that the output stimulation circuitry is configured for generating a current density on the first tissue contacting surface that is greater than the current density on the second tissue contacting surface.

In one embodiment, the neurostimulation system further comprises a lead (e.g., spinal cord stimulation lead) that carries the electrodes. The lead may be, e.g., an in-line lead, in which case, the electrodes are arranged in a single column along the axis of the in-line lead, or a paddle lead, in which case, three of the electrodes may be arranged along a line transverse to the axis of the paddle lead.

In accordance with a third aspect of the present inventions, a neurostimulation lead is provided. The neurostimulation lead comprises an elongated lead body and a plurality of electrodes carried by the lead body. The lead body may be configured for, e.g., being placed adjacent spinal cord tissue. In one embodiment, the electrodes are ring electrodes disposed in a single column around the lead body. In another embodiment, the neurostimulation lead further comprises a paddle disposed on the lead body, in which case, three of the electrodes may be disposed on the paddle along a line transverse to the to the axis of the lead body. The electrodes include first and second electrodes, with the first electrode having a first tissue contacting surface area and the second electrode having a second tissue contact surface area greater than (e.g., at least twice) the first tissue contacting surface area. In one embodiment, the electrodes comprises three columns of electrodes, a center one of the three columns of electrodes has a first total tissue contacting surface, and remaining ones of the three columns of electrodes has a second total tissue contact surface that is less than the first total tissue contacting surface.

Other and further aspects and features of the invention will be evident from reading the following detailed description of the preferred embodiments, which are intended to illustrate, not limit, the invention.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE EMBODIMENTS

At the outset, it is noted that the present invention may be used with an implantable pulse generator (IPG), radio frequency (RF) transmitter, or similar electrical stimulator, that may be used as a component of numerous different types of stimulation systems. The description that follows relates to a spinal cord stimulation (SCS) system. However, it is to be understood that the while the invention lends itself well to applications in SCS, the invention, in its broadest aspects, may not be so limited. Rather, the invention may be used with any type of implantable electrical circuitry used to stimulate tissue. For example, the present invention may be used as part of a pacemaker, a defibrillator, a cochlear stimulator, a retinal stimulator, a stimulator configured to produce coordinated limb movement, a cortical stimulator, a deep brain stimulator, a peripheral nerve stimulator, or in any other neural stimulator configured to treat urinary incontinence, sleep apnea, shoulder sublaxation, etc.

Figure 1:
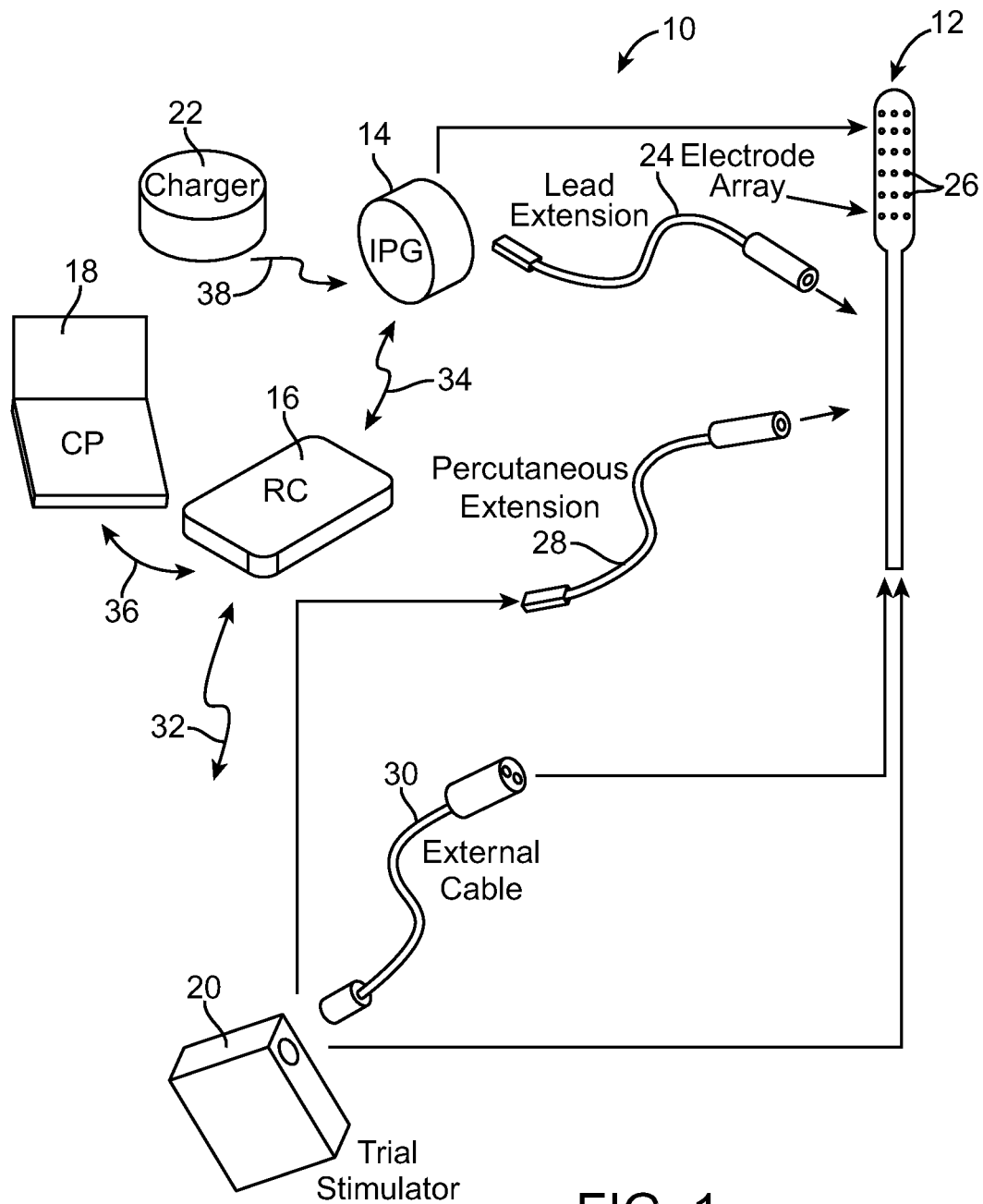
FIG. 1 is plan view of one embodiment of a spinal cord stimulation (SCS) system arranged in accordance with the present inventions.

Turning first to FIG. 1, an exemplary SCS system 10 generally comprises at least one implantable stimulation lead 12, an implantable pulse generator (IPG) 14 (or alternatively RF receiver-stimulator), an external remote control RC 16, a Clinician's Programmer (CP) 18, an External Trial Stimulator (ETS) 20, and an external charger 22.

The IPG 14 is physically connected via one or more lead extensions 24 to the stimulation lead 12, which carries a plurality of electrodes 26 arranged in an array. The stimulation lead 12 is illustrated as a surgical paddle lead in FIG. 1, although as will be described in further detail below, one or more percutaneous stimulation leads can be used in place of the surgical paddle lead 12. As will also be described in further detail below, the IPG 14 includes pulse generation circuitry that delivers electrical stimulation energy in the form of a pulsed electrical waveform (i.e., a temporal series of electrical pulses) to the electrode array 26 in accordance with a set of stimulation parameters.

The ETS 20, which has similar pulse generation circuitry as the IPG 14, also provides electrical stimulation energy to the electrode array 26 in accordance with a set of stimulation parameters. The major difference between the ETS 20 and the IPG 14 is that the ETS 20 is a non-implantable device that is used on a trial basis after the stimulation lead 12 has been implanted and prior to implantation of the IPG 14, to test the effectiveness of the stimulation that is to be provided.

The RC 16 may be used to telemetrically control the ETS 20 via a bi-directional RF communications link 32. Once the IPG 14 and stimulation lead 12 are implanted, the RC 16 may be used to telemetrically control the IPG 14 via a bi-directional RF communications link 34. Such control allows the IPG 14 to be turned on or off and to be programmed with different stimulation programs after implantation. Once the IPG 14 has been programmed, and its power source has been charged or otherwise replenished, the IPG 14 may function as programmed without the RC 16 being present.

The CP 18 provides clinician detailed stimulation parameters for programming the IPG 14 and ETS 20 in the operating room and in follow-up sessions. The CP 18 may perform this function by indirectly communicating with the IPG 14 or ETS 20, through the RC 16, via an IR communications link 36. Alternatively, the CP 18 may directly communicate with the IPG 14 or ETS 20 via an RF communications link (not shown). The external charger 22 is a portable device used to transcutaneously charge the IPG 14 via an inductive link 38.

For purposes of brevity, the details of the RC 16, CP 18, ETS 20, and external charger 22 will not be described herein. Details of exemplary embodiments of these devices are disclosed in U.S. Pat. No. 6,895,280, which is expressly incorporated herein by reference.

Figure 2:
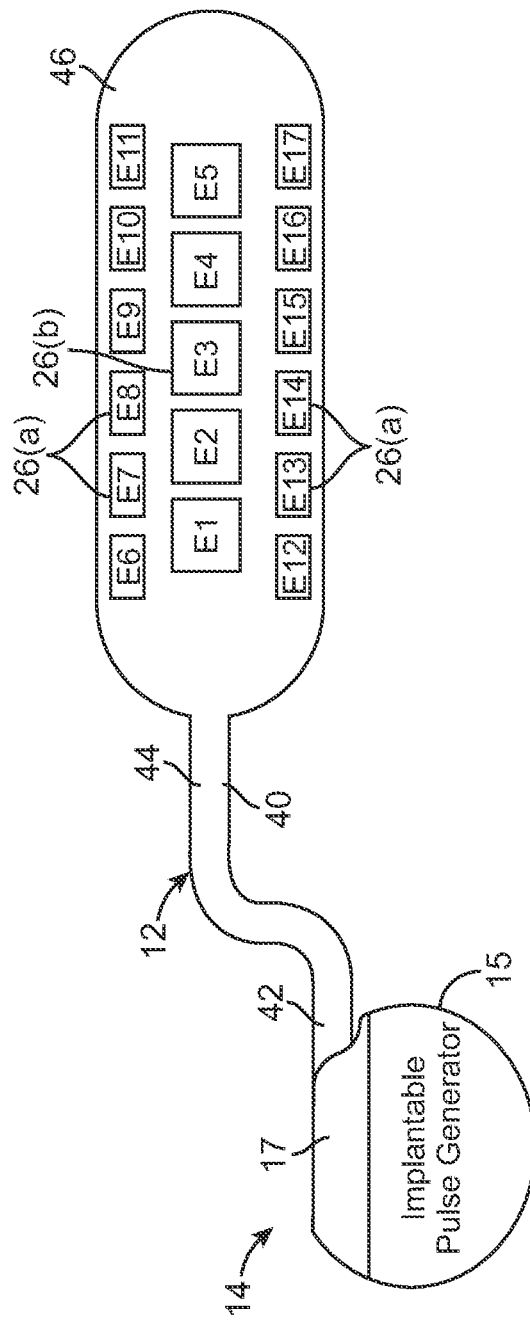
FIG. 2 is a plan view of an implantable pulse generator (IPG) and one embodiment of a stimulation lead used in the SCS system of FIG. 1.

Referring further to FIG. 2, the IPG 14 comprises an outer case 15 for housing the electronic and other components (described in further detail below), and a connector 17 in which the proximal end of the stimulation lead 12 mates in a manner that electrically couples the electrodes 26 to the electronics within the outer case 15. The outer case 15 is composed of an electrically conductive, biocompatible material, such as titanium, and forms a hermetically sealed compartment wherein the internal electronics are protected from the body tissue and fluids. In some cases, the outer case 15 serves as an electrode.

In the embodiment illustrated in FIG. 2, the stimulation lead 12 is a surgical paddle lead that comprises an elongated body 40 having a proximal end 42 and a distal end 44, and a paddle-shaped membrane 46 formed at the distal end 44 of the lead body 40. In an alternative embodiment, the stimulation lead 12 may include multiple elongated bodies, in which case, the paddle-shaped membrane 46 may be formed at the distal ends of the elongated bodies. The lead body 40 may, e.g., have a diameter within the range of 0.03 inches to 0.07 inches and a length within the range of 30 cm to 90 cm for spinal cord stimulation applications. Each lead body 40 may be composed of a suitable electrically insulative material, such as, a polymer (e.g., polyurethane or silicone), and may be extruded from as a unibody construction. The paddle-shaped membrane 46 is composed of an electrically insulative material, such as silicone.

The stimulation lead 12 further comprises a plurality of terminals (not shown) mounted to the proximal end 42 of the lead body 40 and the plurality of electrodes 16 mounted on one side of the paddle-shaped membrane 46 in a two-dimensional arrangement. In the illustrated embodiment, the electrodes 26 are arranged in three columns on one side of the paddle-shaped membrane 46 along the axis of the stimulation lead 12, with the electrodes in the center column being labeled E1-E5, the electrodes in one of the lateral columns (right column when the lead 12 is introduced into the patient in the rostral direction) being labeled E6-E11, and the electrodes in the other of the lateral columns (left column when the lead 12 is introduced into the patient in the rostral direction) being labeled E12-E17. Although the stimulation lead 12 is shown as having seventeen electrodes 26, the number of electrodes may be any number suitable for the application in which the stimulation lead 12 is intended to be used (e.g., three, five, eight, eleven, etc.). Each of the electrodes 26 takes the form of a disk composed of an electrically conductive, non-corrosive, material, such as, e.g., platinum, titanium, stainless steel, or alloys thereof.

The stimulation lead 12 also includes a plurality of electrical conductors (not shown) extending through the lead body 40 and connected between the respective terminals (not shown) and electrodes 26 using suitable means, such as welding, thereby electrically coupling the proximally-located terminals with the distally-located electrodes 26. In the case where the stimulation lead 12 includes multiple elongated bodies, the proximally-located terminals on each lead body will be electrically coupled to a specific column of electrodes 26 located on the paddle-shaped membrane 46 (in this case, the conductors within a first lead body would be coupled to electrodes E1-E5, the conductors within a second lead body would be coupled to electrodes E6-E11, and the conductors within a third lead body would be coupled to electrodes E12-E17).

Further details regarding the construction and method of manufacture of paddle leads are disclosed in U.S. patent application Ser. No. 11/319,291, entitled "Stimulator Leads and Methods for Lead Fabrication," the disclosure of which is expressly incorporated herein by reference.

Significantly, the electrodes 26 include a first set of smaller electrodes 26(a), each of which has a first tissue contacting surface area, and a second set of larger electrodes 26(b), each of which has a second tissue contacting surface area that is greater than the first tissue contacting surface area. In this manner, as will be described in further detail below, the electrical current density at the larger electrodes 26(b) will be decreased relative to the electrical current density at the smaller electrodes 26(a), or conversely, the electrical current density at the smaller electrodes 26(a) will be increased relative to the electrical current density at the larger electrodes 26(b).

Preferably, the second tissue contacting surface area is at least twice as large as the first tissue contacting surface area. In the illustrated embodiment, the second tissue contacting surface area is greater than five times as large as the first tissue contacting surface. In the illustrated embodiment, the center column includes the larger electrodes 26(b), while the two lateral columns include the smaller electrodes 26(a). Each larger electrode 26(b) is centered between four smaller electrodes 26(a). Although the number of smaller electrodes 26(a) is greater than the number of larger electrodes 26(b), in the illustrated embodiment, the total surface area of the larger electrodes 26(b) is greater than the total surface area of the smaller electrodes 26(a).

Figure 3:
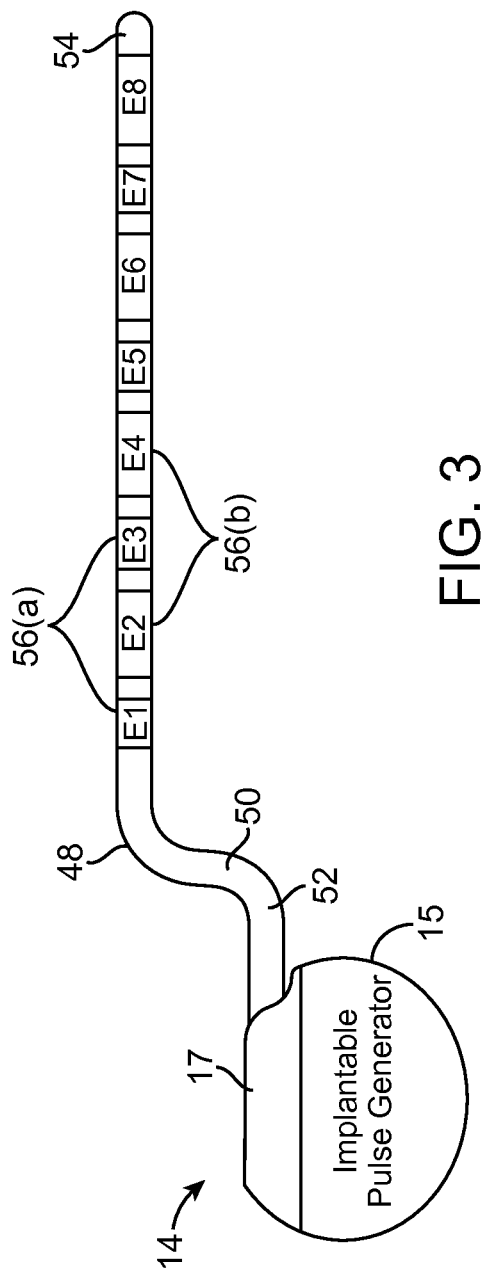
FIG. 3 is a plan view of an implantable pulse generator (IPG) and another embodiment of a stimulation lead used in the SCS system of FIG. 1.

In an alternative embodiment illustrated in FIG. 3, a percutaneous stimulation lead 48 can be used in the SCS system 10 instead of the surgical paddle lead 12. Although only one percutaneous stimulation lead 48 is shown, multiple percutaneous stimulation leads (e.g., two), can be used with the SCS system 10. The stimulation lead 48 includes an elongated lead body 50 having a proximal end 52 and a distal end 54. The lead body 50 may, e.g., have a diameter within the range of 0.03 inches to 0.07 inches and a length within the range of 30 cm to 90 cm for spinal cord stimulation applications. The lead body 50 may be composed of a suitable electrically insulative material, such as, a polymer (e.g., polyurethane or silicone), and may be extruded from as a unibody construction.

The stimulation lead 48 further comprises a plurality of terminals (not shown) mounted to the proximal end 52 of the lead body 50 and a plurality of in-line electrodes 56 (in this case, eight electrodes E1-E8) mounted to the distal end 54 of the lead body 50. Although the stimulation lead 48 is shown as having eight electrodes 56 (and thus, eight corresponding terminals), the number of electrodes may be any number suitable for the application in which the stimulation lead 48 is intended to be used (e.g., two, four, sixteen, etc.). Each of the electrodes 56 takes the form of a cylindrical ring element composed of an electrically conductive, non-corrosive, material, such as, e.g., platinum, titanium, stainless steel, or alloys thereof, which is circumferentially disposed about the lead body 50.

The stimulation lead 48 also includes a plurality of electrical conductors (not shown) extending within the lead body 50 and connected between the respective terminals (not shown) and electrodes 56 using suitable means, such as welding, thereby electrically coupling the proximally-located terminals with the distally-located electrodes 56. The stimulation lead 48 further includes a central lumen (not shown) that may be used to accept an insertion stylet (described in further detail below) to facilitate lead implantation.

Further details describing the construction and method of manufacturing percutaneous stimulation leads are disclosed in U.S. patent application Ser. No. 11/689,918, entitled "Lead Assembly and Method of Making Same," and U.S. patent application Ser. No. 11/565,547, entitled "Cylindrical Multi-Contact Electrode Lead for Neural Stimulation and Method of Making Same," the disclosures of which are expressly incorporated herein by reference.

Significantly, the electrodes 56 include a first set of smaller electrodes 56(a), each of which has a first tissue contacting surface area, and a second set of larger electrodes 56(b), each of which has a second tissue contacting surface area that is greater than the first tissue contacting surface area. In the same manner described above with respect to the electrodes 26, the electrical current density at the larger electrodes 56(b) will be decreased relative to the electrical current density at the smaller electrodes 56(a), or conversely, the electrical current density at the smaller electrodes 56(a) will be increased relative to the electrical current density at the larger electrodes 56(b). Again, the second tissue contacting surface area is at least twice as large as the first tissue contacting surface area. In the illustrated embodiment, equal numbers of smaller electrodes 56(a) and larger electrodes 56(b) extend along the axis of the stimulation lead 48 in an alternating fashion.

As will be described in further detail below, the IPG 14 includes pulse generation circuitry that provides electrical conditioning and stimulation energy to the electrodes 26 (or alternatively the electrodes 56) in accordance with a set of parameters. Such parameters may comprise electrode combinations, which define the electrodes that are activated as anodes (positive), cathodes (negative), and turned off (zero), and electrical pulse parameters, which define the pulse amplitude (measured in milliamps or volts depending on whether the IPG 14 supplies constant current or constant voltage to the electrodes), pulse duration (measured in microseconds), and pulse rate (measured in pulses per second).

With respect to the pulse patterns provided during operation of the SCS system 10, electrodes that are selected to transmit or receive electrical energy are referred to herein as "activated," while electrodes that are not selected to transmit or receive electrical energy are referred to herein as "non-activated." Electrical energy delivery will occur between two (or more) electrodes, one of which may be the IPG case, so that the electrical current has a path from the energy source contained within the IPG case to the tissue and a sink path from the tissue to the energy source contained within the case. Electrical energy may be transmitted to the tissue in a monopolar or multipolar (e.g., bipolar, tripolar, etc.) fashion.

Monopolar delivery occurs when a selected one or more of the lead electrodes is activated along with the case of the IPG 14, so that electrical energy is transmitted between the selected electrode and case. Monopolar delivery may also occur when one or more of the lead electrodes are activated along with a large group of lead electrodes located remotely from the one more lead electrodes so as to create a monopolar effect; that is, electrical energy is conveyed from the one or more lead electrodes in a relatively isotropic manner. Bipolar delivery occurs when two of the lead electrodes are activated as anode and cathode, so that electrical energy is transmitted between the selected electrodes. Tripolar delivery occurs when three of the lead electrodes are activated, two as anodes and the remaining one as a cathode, or two as cathodes and the remaining one as an anode.

Figure 4:
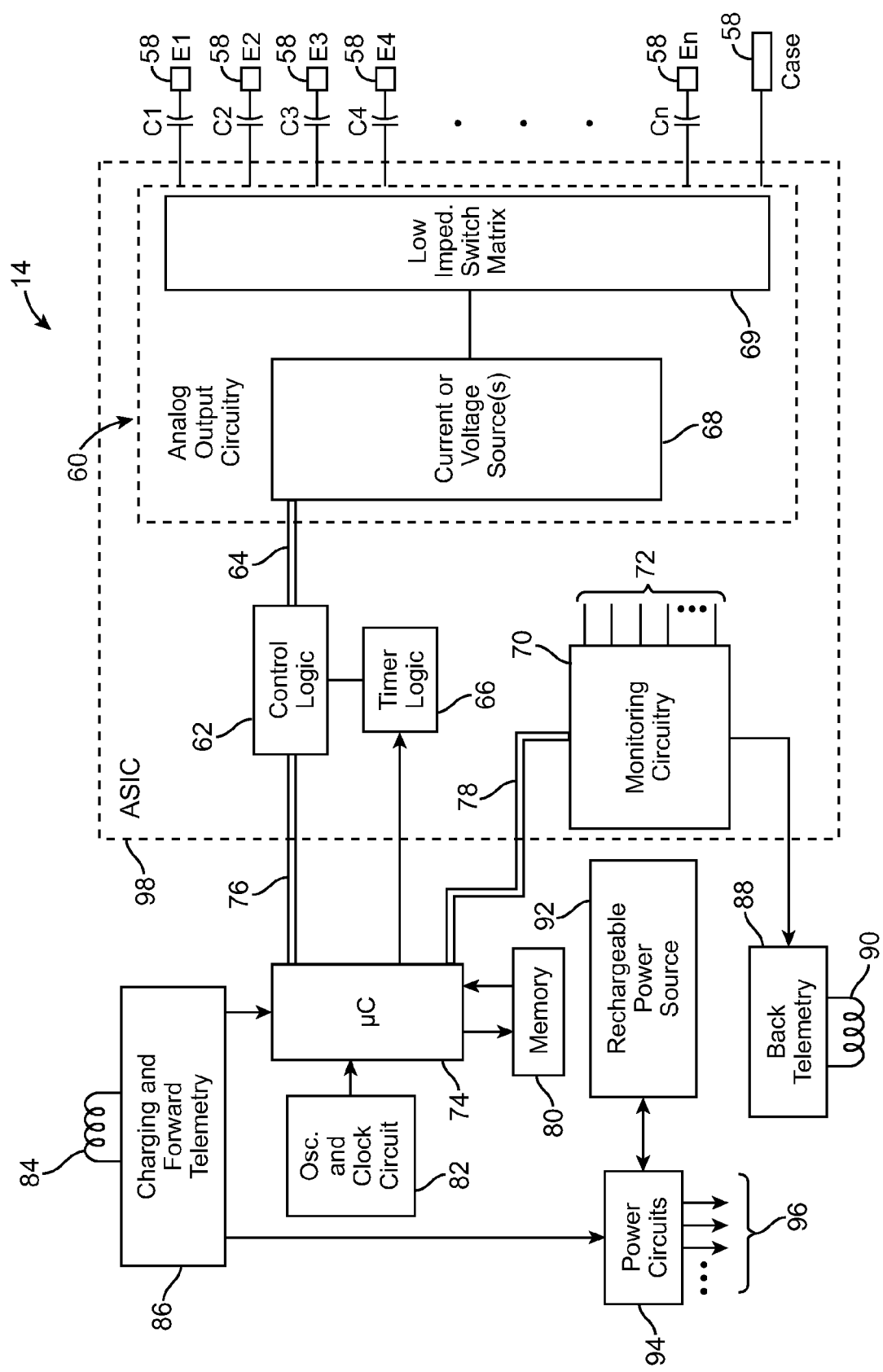
FIG. 4 is a block diagram of the internal components of the IPG of FIG. 1.

Turning next to FIG. 4, the main internal components of the IPG 14 will now be described. The IPG 14 includes analog output circuitry 60 capable of individually generating electrical stimulation pulses via capacitors C1-Cn at the electrodes 26 (or alternatively the electrodes 56) (E1-En) of specified amplitude under control of control logic 62 over data bus 64. The duration of the electrical stimulation (i.e., the width of the stimulation pulses), is controlled by the timer logic 66.

Because the present invention lends itself well to simplistic electrical energy delivery systems, the analog output circuitry 60 comprises one or more current or voltage sources 68. The one or more current or voltage sources 68 can be, e.g., either a single current source for sourcing and sinking electrical pulses of a specified and known amperage to and from the electrodes 26, or a single voltage source for sourcing and sinking electrical pulses of a specified and known voltage to or from the electrodes 26. However, in alternative embodiments, the analog output circuitry 60 may comprise independently controlled current sources for sourcing and sinking electrical pulses of a specified and known amperage to or from the electrodes 26, or independently controlled voltage sources for sourcing or sinking electrical pulses of a specified and known voltage to or from the electrodes 26.

In any event, the analog output circuitry 60 includes a switch matrix 69 coupled between the electrodes 26 and the power source, such that selected ones of the electrodes 26 can be configured as cathodes (by coupling them to a negative terminal of the source(s) 68) and selected ones of the electrodes 26 can be configured as anodes (by coupling them to a positive terminal of the source(s) 68).

The IPG 14 further comprises monitoring circuitry 70 for monitoring the status of various nodes or other points 72 throughout the IPG 14, e.g., power supply voltages, temperature, battery voltage, and the like. The IPG 14 further comprises processing circuitry in the form of a microcontroller 74 that controls the control logic 62 over data bus 76, and obtains status data from the monitoring circuitry 70 via data bus 78. The IPG 14 additionally controls the timer logic 66. The IPG 14 further comprises memory 80 and oscillator and clock circuit 82 coupled to the microcontroller 74. The microcontroller 74, in combination with the memory 80 and oscillator and clock circuit 82, thus comprise a microprocessor system that carries out a program function in accordance with a suitable program stored in the memory 80. Alternatively, for some applications, the function provided by the microprocessor system may be carried out by a suitable state machine.

Thus, the microcontroller 74 generates the necessary control and status signals, which allow the microcontroller 74 to control the operation of the IPG 14 in accordance with a selected operating program and parameters. In controlling the operation of the IPG 14, the microcontroller 74 is able to individually generate electrical pulses at the electrodes 26 using the analog output circuitry 60, in combination with the control logic 62 and timer logic 66, thereby allowing each electrode 26 to be paired or grouped with other electrodes 26, including the monopolar case electrode, and to control the polarity, amplitude, rate, and pulse width through which the current stimulus pulses are provided.

The IPG 14 further comprises an alternating current (AC) receiving coil 84 for receiving programming data (e.g., the operating program and/or stimulation parameters) from the RC 16 in an appropriate modulated carrier signal, and charging and forward telemetry circuitry 86 for demodulating the carrier signal it receives through the AC receiving coil 84 to recover the programming data, which programming data is then stored within the memory 80, or within other memory elements (not shown) distributed throughout the IPG 14.

The IPG 14 further comprises back telemetry circuitry 88 and an alternating current (AC) transmission coil 90 for sending informational data sensed through the monitoring circuitry 70 to the RC 16. The back telemetry features of the IPG 14 also allow its status to be checked. For example, any changes made to the stimulation parameters are confirmed through back telemetry, thereby assuring that such changes have been correctly received and implemented within the IPG 14. Moreover, upon interrogation by the RC 16, all programmable settings stored within the IPG 14 may be uploaded to the RC 16.

The IPG 14 further comprises a rechargeable power source 92 and power circuits 94 for providing the operating power to the IPG 14. The rechargeable power source 92 may, e.g., comprise a lithium-ion or lithium-ion polymer battery. The rechargeable battery 92 provides an unregulated voltage to the power circuits 94. The power circuits 94, in turn, generate the various voltages 96, some of which are regulated and some of which are not, as needed by the various circuits located within the IPG 14. The rechargeable power source 92 is recharged using rectified AC power (or DC power converted from AC power through other means, e.g., efficient AC-to-DC converter circuits, also known as "inverter circuits") received by the AC receiving coil 84. To recharge the power source 92, an external charger (not shown), which generates the AC magnetic field, is placed against, or otherwise adjacent, to the patient's skin over the implanted IPG 14. The AC magnetic field emitted by the external charger induces AC currents in the AC receiving coil 84. The charging and forward telemetry circuitry 86 rectifies the AC current to produce DC current, which is used to charge the power source 92. While the AC receiving coil 84 is described as being used for both wirelessly receiving communications (e.g., programming and control data) and charging energy from the external device, it should be appreciated that the AC receiving coil 84 can be arranged as a dedicated charging coil, while another coil, such as coil 90, can be used for bi-directional telemetry.

It should be noted that the diagram of FIG. 4 is functional only, and is not intended to be limiting. Those of skill in the art, given the descriptions presented herein, should be able to readily fashion numerous types of IPG circuits, or equivalent circuits, that carry out the functions indicated and described. It should be noted that rather than an IPG, the SCS system 10 may alternatively utilize an implantable receiver-stimulator (not shown) connected to the stimulation lead 12. In this case, the power source, e.g., a battery, for powering the implanted receiver, as well as control circuitry to command the receiver-stimulator, will be contained in an external controller inductively coupled to the receiver-stimulator via an electromagnetic link. Data/power signals are transcutaneously coupled from a cable-connected transmission coil placed over the implanted receiver-stimulator. The implanted receiver-stimulator receives the signal and generates the stimulation in accordance with the control signals.

Figure 5:
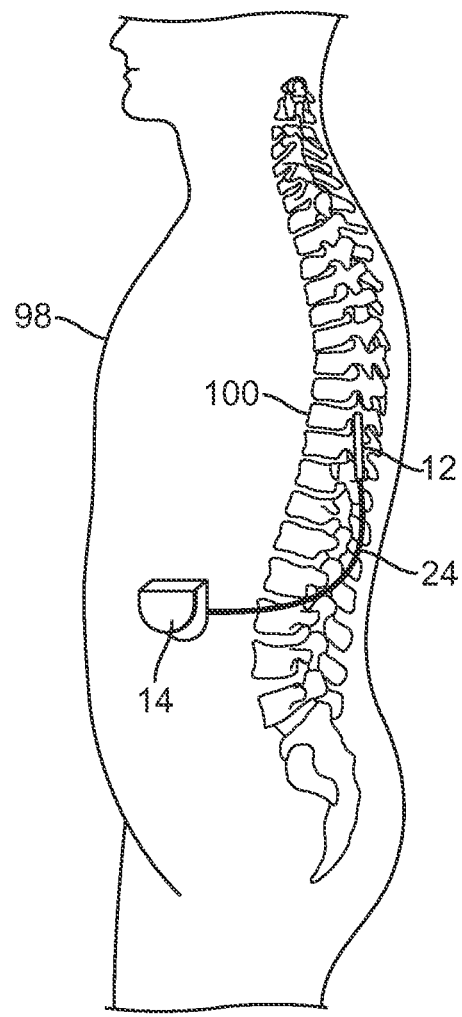
FIG. 5 is a plan view of the SCS system of FIG. 1 in use with a patient.

Referring to FIG. 5, the stimulation lead 12 (or alternatively the stimulation lead 48) is implanted within the spinal column 100 of a patient 98. The preferred placement of the stimulation lead 12 is adjacent, i.e., resting upon, the spinal cord area to be stimulated. Due to the lack of space near the location where the stimulation lead 12 exit the spinal column 100, the IPG 14 is generally implanted in a surgically-made pocket either in the abdomen or above the buttocks. The IPG 14 may, of course, also be implanted in other locations of the patient's body. The lead extension 24 facilitates locating the IPG 14 away from the exit point of the stimulation lead 12. After implantation, the IPG 14 is used to provide the therapeutic stimulation under control of the patient. The electrodes 26 may be arranged medio-laterally with respect to the spinal cord, or alternatively, the electrodes 56 may be arranged rostro-caudally with respect to the spinal cord.

Figure 6:
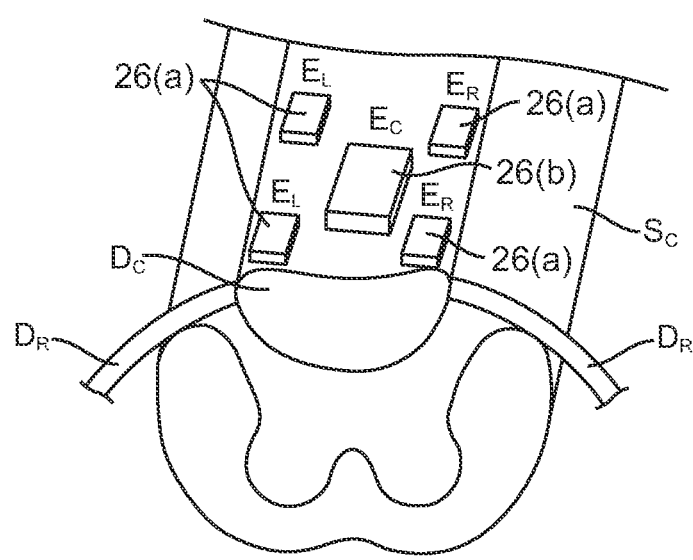
FIG. 6 is a perspective view of the electrodes of the stimulation lead of FIG. 2 medio-laterally located over the spinal cord of a patient.

For example, as shown in FIG. 6, the surgical lead 12 illustrated in FIG. 2 can be used to arrange five electrodes 26 (one center electrode $E_C$ located over the center of the dorsal column DC nerve fibers, two left electrodes $E_L$ laterally placed from the center of the DC nerve fibers adjacent the left dorsal root DR nerve fibers, and two right electrodes $E_R$ laterally placed from the center of the dorsal column DC nerve fibers adjacent the right dorsal root DR nerve fibers) transverse to the axis of the spinal cord SC (medio-laterally). As there shown, the larger electrode 26(b) is the center electrode $E_C$, while the smaller electrodes 26(a) are the left and right electrodes $E_L$, $E_R$.

Figure 7:
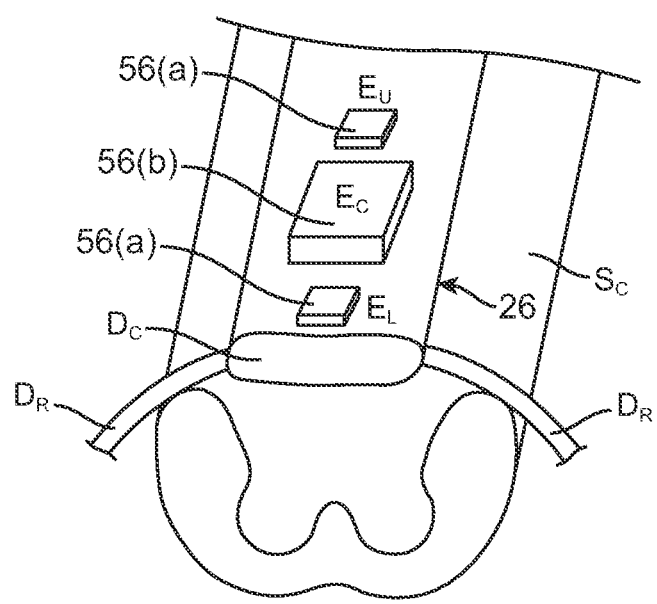
FIG. 7 is a perspective view of the electrodes of the stimulation lead of FIG. 3 rostro-caudally located over the spinal cord of a patient.

As another example, as shown in FIG. 7, the percutaneous lead 48 illustrated in FIG. 3 can be used to arrange three electrodes 26 (an upper (or rostral) electrode $E_U$, a center electrode $E_C$, and a lower (or caudal) electrode $E_L$) along the axis of the spinal cord SC (rostro-caudally) over the dorsal column DC nerve fibers. As there shown, the larger electrode 56(b) is the center electrode $E_C$, while the smaller electrodes 56(a) are the upper and lower electrodes $E_U$, $E_L$.

The SCS system 10 has application in a wide variety of electrical stimulation regimens.

Figure 9:
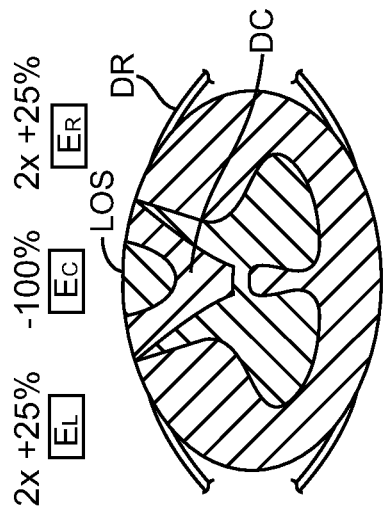
FIG. 9 is a cross-section diagram of a spinal cord, particularly illustrating a locus of stimulation induced by the medio-lateral electrode arrangement of FIG. 7.
Figure 8:
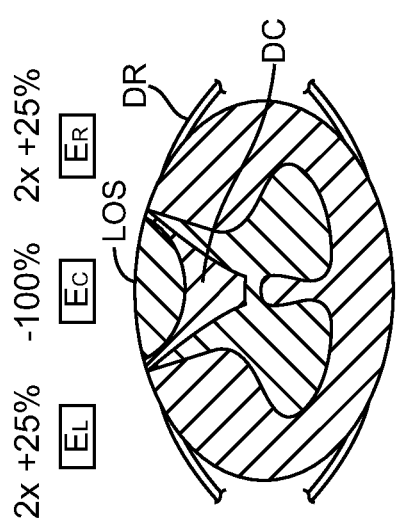
FIG. 8 is a cross-section diagram of a spinal cord, particularly illustrating a locus of stimulation induced by a prior art medio-lateral electrode arrangement.

For example, neurostimulation regimens that use the surgical paddle lead 12 to medio-laterally arrange the electrodes 26 in the manner illustrated in FIG. 6 can be used to shape of the AP generating neural region of the spinal cord in order to prevent the generation of APs in non-target neural fibers. As shown in FIGS. 8 and 9, the center electrode $E_C$ is placed over the dorsal column DC nerve fibers, while the two left electrodes $E_L$ (only one shown) and the two right electrodes $E_R$ (only one shown) are respectively placed over the dorsal root DR nerve fibers on both sides of the dorsal column DC nerve fibers.

A conventional stimulation regimen that uses uniformly sized electrodes will serve as a reference for the stimulation regimens performed in accordance with the present inventions, and will thus be initially described with reference to FIG. 8. In this conventional stimulation regimen, the left and right electrodes $E_L$ (2 each) and $E_R$ (2 each) are activated as anodes and the center electrode $E_C$ is activated as a cathode. In the illustrated embodiment, the four electrodes $E_L$, $E_R$ are each sourcing 25% of the total current (e.g., 1 mA each) the center electrode $E_C$ is sinking 100% of the total current (e.g., 4 mA). The combination of the hyperpolarizing electric fields generated by the left and right electrodes $E_L$, $E_R$ and the depolarizing electric field generated by the center electrode $E_C$ results in an area within the dorsal column DC that is at or above the depolarization threshold. This area, which has an overall depth and width, is the locus of stimulation LOS.

In the conventional stimulation regimen described above, it is desirable that the locus of stimulation LOS be as narrow as possible without increasing the depth of the LOS, thereby stimulating target nerve fibers within the dorsal column DC, while preventing stimulation of non-target nerve fibers within the dorsal roots DR. This would require an increase in the hyperpolarizing electrical field generated by the left and right electrodes $E_L$, $E_R$ over that illustrated in FIG. 8. That is, strengthening of the hyperpolarizing electric fields created by the electrodes $E_L$, $E_R$ tends to result in a narrowing the locus of stimulation LOS because it weakens the lateral edges of the depolarizing electric field created by the center electrode $E_C$. However, this necessarily may result in an increase in the current sunk by the center electrode $E_C$, thereby increasing the depth of the locus of stimulation LOS, which may lead to undesirable outcomes (e.g., discomfort or undesirable reflexive activity).

The SCS system 10 may be used to solve this problem by effectively increasing the AP threshold of the dorsal root DR nerve fibers relative to the AP threshold of the dorsal column DC nerve fibers. As illustrated in FIG. 9, one example of a stimulation regimen in accordance with a present invention involves creating a locus of stimulation LOS that has a smaller width and the same depth. Here, in the same manner described above with respect to FIG. 8, the left and right electrodes $E_L$, $E_R$ are activated as anodes and the center electrode $E_C$ is activated as a cathode. However, the amount of current sourced at the left and right electrodes $E_L$, $E_R$ should be sufficient to create a hyperpolarizing electric field that is strong enough to narrow the locus of stimulation LOS to the smaller width. For example, the current sourced at the left and right electrodes $E_L$, $E_R$ may be increased (e.g., 4-8 mA each) in order to strengthen the hyperpolarizing electric fields.

Notably, if the sizes of the electrodes $E_L$, $E_R$, $E_C$ were the same, sinking all of the current sourced by the left and right electrodes $E_L$, $E_R$ at the center electrode $E_C$ could result in a depolarizing electric field that would undesirably increase the depth of the locus of stimulation LOS. However, because center electrode $E_C$ has an increased tissue contacting surface area, the decreased current density will compensate for the increased current at the center electrode $E_C$, thereby allowing the intensity of the depolarizing electric field created by the center electrode $E_C$ to be reduced to a level that does not increase the depth of the locus of stimulation LOS compared to that illustrated in FIG. 8.

Alternatively, rather the narrowing the locus of stimulation LOS in both directions, the locus of stimulation LOS may be narrowed in only one direction. Here, only one of left and right electrodes $E_L$, $E_R$ is activated as an anode. In this case, 100% of the total current is being sourced at the left electrode $E_L$ or right electrode $E_R$, and 100% of the total current is being sunk at the center electrode $E_C$.

Figure 10:
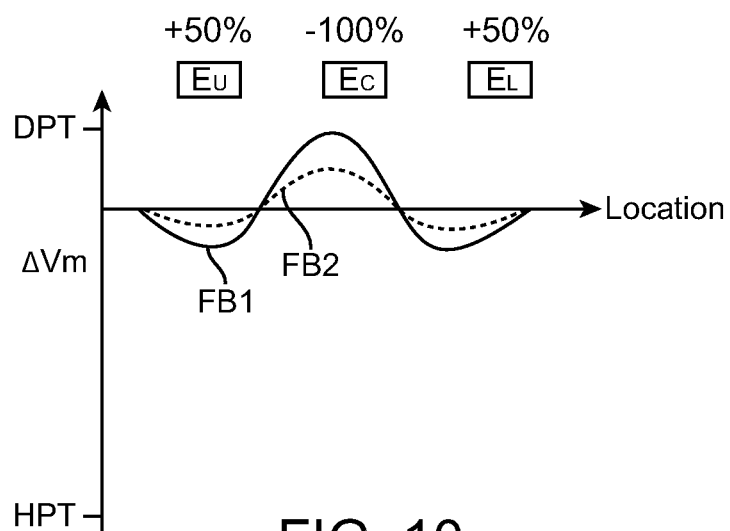
FIG. 10 is a graph of the changes in neural fiber transmembrane potential in first and second fibers bundles induced by a prior art rostro-caudal electrode arrangement.
Figure 11:
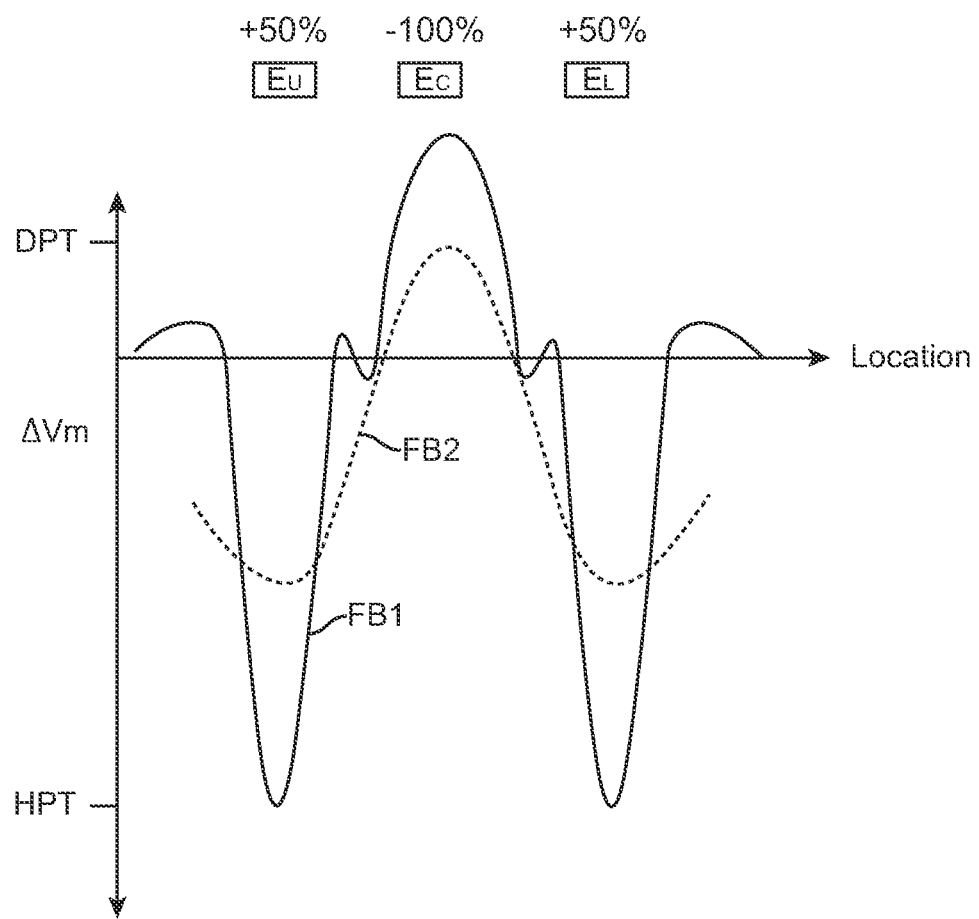
FIG. 11 is a graph of the changes in neural fiber transmembrane potential in first and second fibers bundles induced by the rostro-caudal electrode arrangement of FIG. 8.

As another example, neurostimulation regimens that use the percutaneous lead 48 to rostro-caudally arrange the electrodes 56 in the manner illustrated in FIG. 7 can be used to selectively block APs in neural fibers. As shown in FIGS. 10 and 11, the changes in transmembrane potential ($\Delta V_m$) of neural fibers in fiber bundles that are in the vicinity of the electrodes 56 of the percutaneous lead 48 are graphically illustrated when electric fields are generated by the electrodes 56 during the neurostimulation regimens. The neurostimulation regimens are discussed in the context of first and second fiber bundles FB1 and FB2. In the illustrated examples, the first fiber bundle FB1 is the closest fiber bundle to the electrodes 56, and the second fiber bundle FB2 is the next closest fiber bundle to the electrodes 56.

A conventional stimulation regimen that uses uniformly sized electrodes will serve as a reference for the stimulation regimens performed in accordance with the present inventions, and will thus be initially described with reference to FIG. 10. In this conventional stimulation regimen, the upper and lower electrodes $E_U$, $E_L$ are activated as anodes, and the center electrode $E_C$ is activated as a cathode. In the illustrated embodiment, 50% of the total current (e.g., 2 mA) is being sourced at each of the upper and lower electrodes $E_U$, $E_L$, and 100% of the total current (e.g., 2 mA) is being sunk at the center electrode $E_C$.

The depolarizing electric field generated by the center electrode $E_C$ is sufficient to create APs in some of the neural fibers in the first fiber bundle FB1. In other words, the depolarization threshold DPT has been met for the first fiber bundle FB1 in the tissue adjacent the center electrode $E_C$. The depolarizing electric field generated by the center electrode $E_C$ is substantially weaker at the second fiber bundle FB2 and is below the AP-creating depolarization threshold DPT. The locus of stimulation is, therefore, defined by the portion of the depolarizing electric field generated by the center electrode $E_C$ that is at or above the depolarization threshold DPT.

The upper and lower electrodes $E_U$, $E_L$, which are functioning as anodes in the stimulation regimen illustrated in FIG. 10, will create hyperpolarizing electric fields in the neural tissue adjacent the upper and lower electrodes $E_U$, $E_L$. When the electric field is at or above the hyperpolarization threshold HPT, the neural fibers within the electric field will block APs that were fired at other points along the fibers. It should be noted here that the magnitude of the hyperpolarization threshold HPT has been estimated to be about 2 to 8 times the magnitude of the depolarization threshold DPT. The hyperpolarizing electric fields generated by upper and lower electrodes $E_U$ and $E_L$ in the exemplary stimulation regimen are below the hyperpolarization threshold HPT at the first fiber bundle FB1. As such, APs in the fiber bundle FB1 that fired at points in the neural fibers adjacent to center electrode $E_C$ will not be blocked at points adjacent the upper and lower electrodes $E_U$, $E_L$. The hyperpolarizing electric fields generated by the upper and lower electrodes $E_U$, $E_L$ will, of course, be even weaker at the second fiber bundle FB2.

In the conventional stimulation regimen described above, the generation of APs in the fibers within the second fiber bundle FB2 will require an increase in the depolarizing electric field generated by the center electrode $E_C$ over that illustrated in FIG. 10. There may be instances where the generation of APs in the first fiber bundle FB1, which necessarily results from the creation of a depolarizing electric field that is strong enough to meet the depolarization threshold DPT at the second fiber bundle FB2, may lead to undesirable outcomes (e.g. discomfort or undesirable reflexive activity) for the patient.

The SCS system 10 may be used to solve this problem by preventing APs generated in the first fiber bundle FB1 from reaching the brain or end organ. Specifically, as illustrated in FIG. 11, one example of a stimulation regimen in accordance with the present invention involves creating local AP blocks that prevent APs created within a portion of the depolarizing electric field that is at or above the depolarization threshold DPT from traveling in both directions beyond the stimulation site. The effective locus of stimulation is, therefore, the region of neural fibers that are generating APs that are not blocked at other portions of the stimulation site.

Here, in the same manner described above with respect to FIG. 10, the upper and lower electrodes $E_U$, $E_L$ are activated as anodes and the center electrode $E_C$ is activated as a cathode. However, the amount of current sunk at the center electrode $E_C$ is sufficient to create a depolarizing electric field that is strong enough to meet the depolarization threshold DPT at the second fiber bundle FB2 and cause fibers within the second fiber bundle to generate APs. Such a depolarizing electric field will, of course, also cause the fibers in the first fiber bundle FB1 to generate APs.

However, at least a substantial portion of the APs in the first fiber bundle FB1 will be prevented from passing electrode EU by the hyperpolarization. In particular, at least a substantial portion of the APs (i.e., >10-20%) are blocked by hyperpolarizing tissue in the first fiber bundle FB1, located on opposite sides of the tissue in the first fiber bundle FB1 that is generating the APs, to at least the hyperpolarization threshold HPT. This may be accomplished by significantly increasing the level of current sourced from the upper and lower electrodes $E_U$, $E_L$, as compared to the level illustrated in FIG. 10 (e.g., about 2.5 mA each), in order to reach the hyperpolarization threshold HPT within the first fiber bundle FB1 at the upper and lower electrodes $E_U$, $E_L$.

Notably, if the sizes of the electrodes $E_U$, $E_C$, $E_L$ were the same, sinking all of the current sourced by the upper and lower electrodes $E_U$ and $E_L$ at the center electrode $E_C$ could result in a depolarizing electric field that would meet or exceed the depolarization threshold DPT in fiber bundles well beyond the second fiber bundle FB2. However, because the center electrode $E_C$ has an increased tissue contacting surface area, the decreased current density will compensate for the increased current at the center electrode $E_C$, thereby allowing the intensity of the depolarizing electric field created by the center electrode $E_C$ to be reduced to a level where the depolarization threshold DPT will not be met in fibers beyond the second fiber bundle FB2.

Alternatively, rather the blocking AP in both directions, the stimulation regimen may involve locally blocking APs in a single direction generated in the first fiber bundle FB1. Here, only one of upper and lower electrodes $E_U$, $E_L$ is activated as an anode. In this case, 100% of the total current is being sourced at the upper electrode $E_U$ or lower electrode $E_L$, and 100% of the total current is being sunk at the center electrode $E_C$.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A method of providing therapy to a patient, comprising:
    placing a plurality of electrodes adjacent to tissue of the patient, the electrodes including first and second electrodes, the first electrode having a first tissue contacting surface area and the second electrode having a second tissue contacting surface area greater than the first tissue contacting surface area; and
    simultaneously sourcing anodic electrical current from the first electrode to a first tissue site, thereby increasing an action potential threshold at the first tissue site, and sinking cathodic electrical current from a second tissue site to the second electrode, thereby providing the therapy to the patient.

2. The method of claim 1, wherein electrical current is conveyed between the first and second electrodes to source the anodic electrical current from the first electrode and sink the cathodic electrical current to the second electrode.

3. The method of claim 1, wherein the second tissue contacting surface area is at least twice the first tissue contacting surface area.

4. The method of claim 1, wherein the current density on the first tissue contacting surface is greater than the current density on the second tissue contacting surface.

5. The method of claim 1, wherein the anodic electrical current and cathodic electrical current comprises a plurality of electrical pulses.

6. The method of claim 1, wherein the tissue is spinal cord tissue.

7. The method of claim 6, wherein the electrodes are arranged medio-laterally along the spinal cord tissue.

8. The method of claim 7, wherein the second tissue site is located on dorsal column neural fibers of the spinal cord tissue, the first tissue site is located on dorsal root neural fibers of the spinal cord tissue, the sunk cathodic electrical current generates action potentials in the dorsal column neural fibers to provide the therapy to the patient, and the sourced anodic electrical current increases the action potential threshold of the at least one dorsal root neural fiber.

9. The method of claim 6, wherein the electrodes are arranged rostro-caudally along the spinal cord tissue.

10. The method of claim 9, wherein each of the first and second tissue sites are located on dorsal column neural fibers of the spinal cord tissue, the second electrode is a first distance from the first tissue site and is a second greater distance from the second tissue site, the sunk cathodic electrical current generates action potentials at the first tissue site, and generates additional action potentials at the second tissue site to provide therapy to the patient, and the sourced anodic electrical current blocks at least some of the action potentials at the first site.

* * * * *